United States Patent
Barabash et al.

[11] Patent Number: 6,138,513
[45] Date of Patent: Oct. 31, 2000

[54] METHOD AND APPARATUS FOR FAST ACQUISITION OF ULTRASOUND IMAGES

[76] Inventors: Leonid S. Barabash, 15226 S. Power Rd., Apt 2006, Higley, Ariz. 85236; Aaron E. LaBarge, 3914 E. Namde St., Phoenix, Ariz. 85044

[21] Appl. No.: 09/228,028

[22] Filed: Jan. 9, 1999

[51] Int. Cl.[7] ............................. A61B 8/00; G03B 42/06
[52] U.S. Cl. .............................. 73/602; 73/626; 600/447; 600/443; 367/105; 367/905; 367/138; 367/7; 367/11
[58] Field of Search .................... 73/559, 600, 602, 73/625, 626, 627, 628, 641, 642; 702/39, 194; 600/443, 442, 447, 437; 367/138, 905, 11, 7, 87, 103, 105

[56] References Cited

U.S. PATENT DOCUMENTS

| | | | |
|---|---|---|---|
| 4,784,147 | 11/1988 | Moshfeghi | 128/653 |
| 4,815,047 | 3/1989 | Hart | 367/103 |
| 4,841,492 | 6/1989 | Russell | 367/105 |
| 5,349,359 | 9/1994 | Dallaire et al. | 342/195 |
| 5,549,111 | 8/1996 | Wright et al. | 128/742 |
| 5,581,517 | 12/1996 | Gee et al. | 367/138 |
| 5,617,862 | 4/1997 | Cole et al. | 128/661.01 |
| 5,673,697 | 10/1997 | Bryan et al. | 128/660.07 |
| 5,675,554 | 10/1997 | Cole et al. | 367/138 |
| 5,685,308 | 11/1997 | Wright et al. | 128/660.07 |
| 5,795,297 | 8/1998 | Daigle | 600/447 |
| 5,797,845 | 8/1998 | Barabash et al. | 600/443 |
| 5,860,926 | 1/1999 | Barabash et al. | 600/443 |
| 5,951,479 | 9/1999 | Holm et al. | 600/447 |

OTHER PUBLICATIONS

Gordon S. Kino, Acoustic Waves, Printice–Hall, Englewood, NJ, 07.632, 1987, p. 389.

S.W.Smith et al., Two–Dimensional Arrays for Medical Ultrasound, Ultrasonics Symposium, 1991, pp. 625–628.

*Primary Examiner*—Hezron Williams
*Assistant Examiner*—Rose M. Miller

[57] ABSTRACT

New apodization functions providing an effective rejection of side lobe amplitude level within wide range of beam steering angles are described in this invention. A central amplitude apodization function (13) reduces amplitudes for the central section of transmit and receive array individual elements. A time apodization function (14) changes a duration of transmit pulses. A duration of transmit pulses is short for central section of transmit array and increases for outlying transmit individual elements. A frequency apodization function (15) changes frequency of transmit pulses for different transmit individual elements. The use of new apodization function allows realization of portable acoustic scanners. Some versions of a portable acoustic scanner design and a version with time compression of echo signals are described.

8 Claims, 8 Drawing Sheets

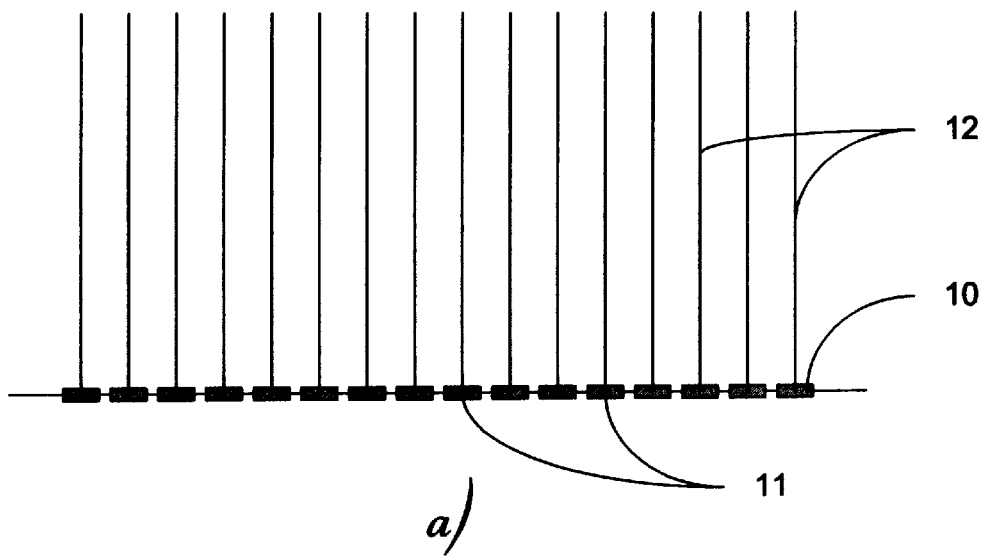
a)
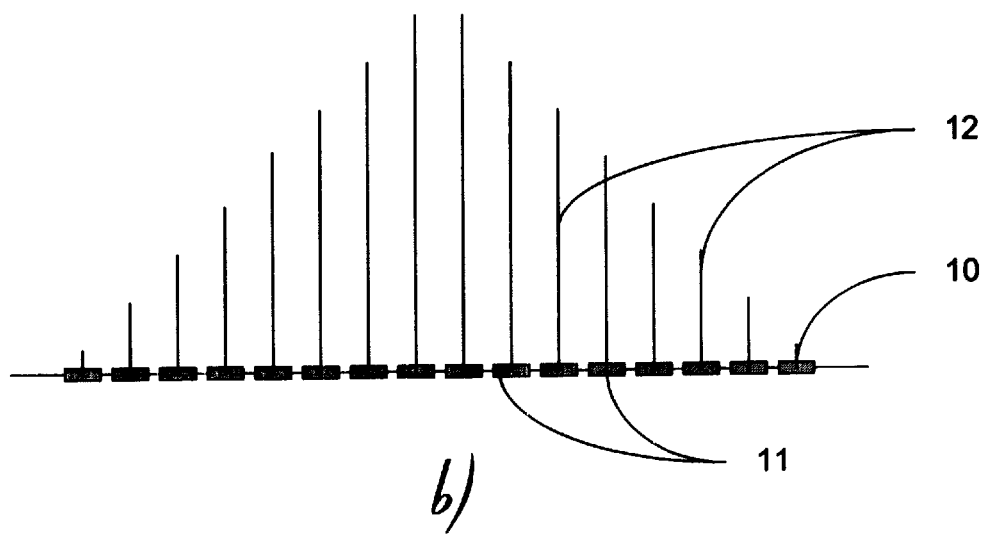
b)
Figure 1

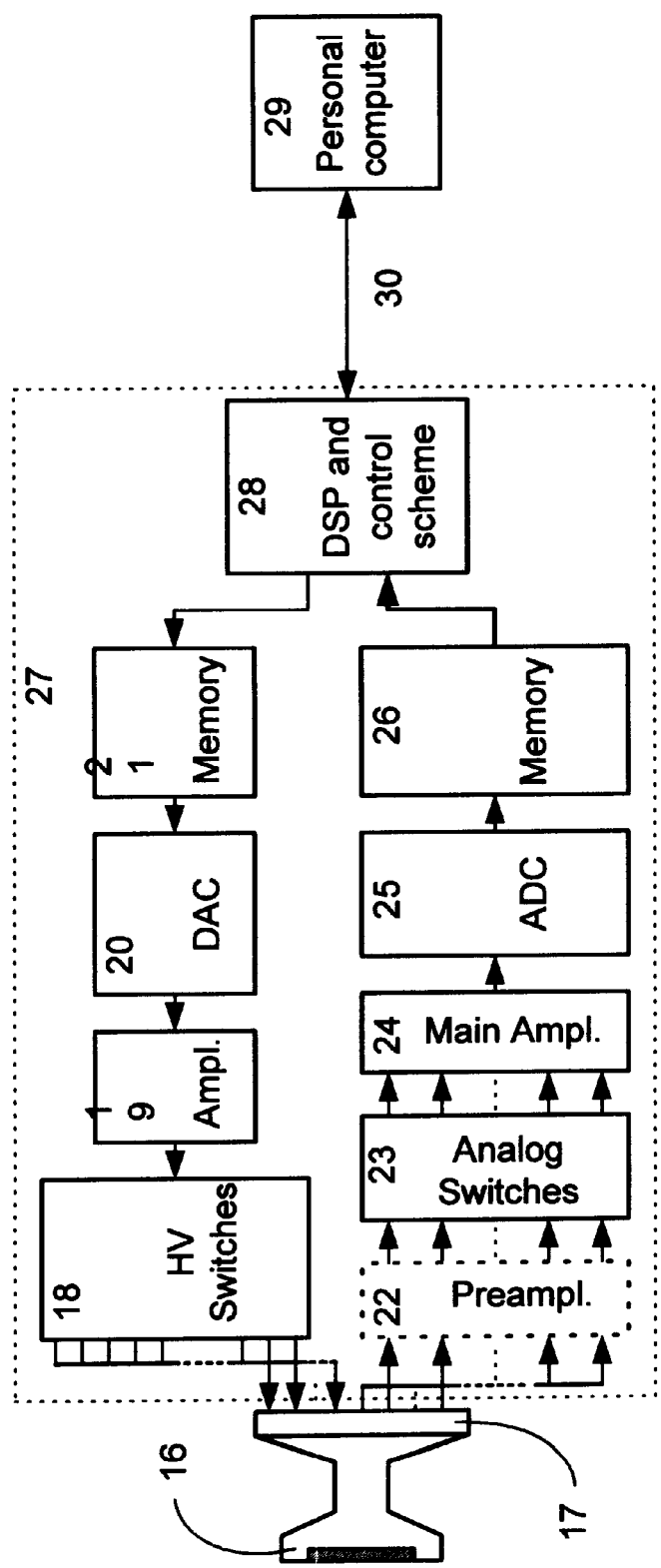
Figure 3.a

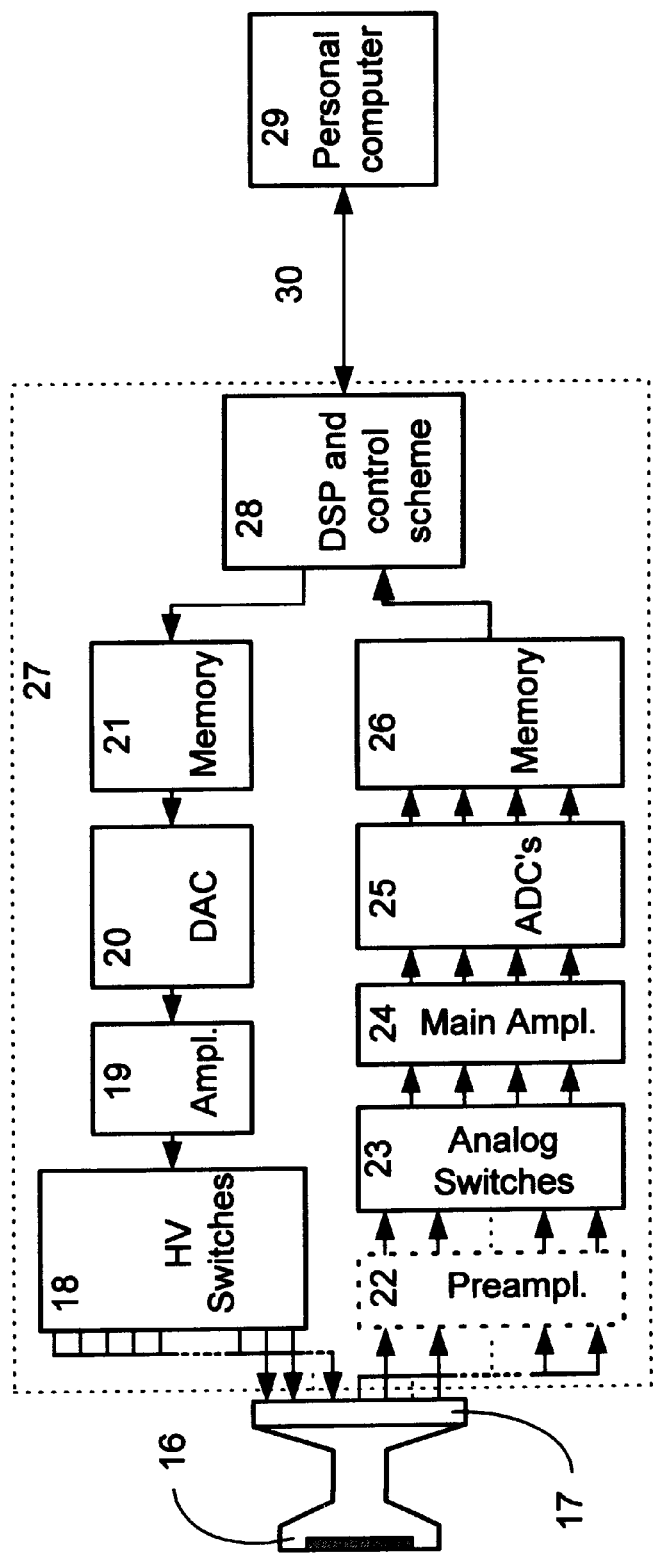
Figure 3.b

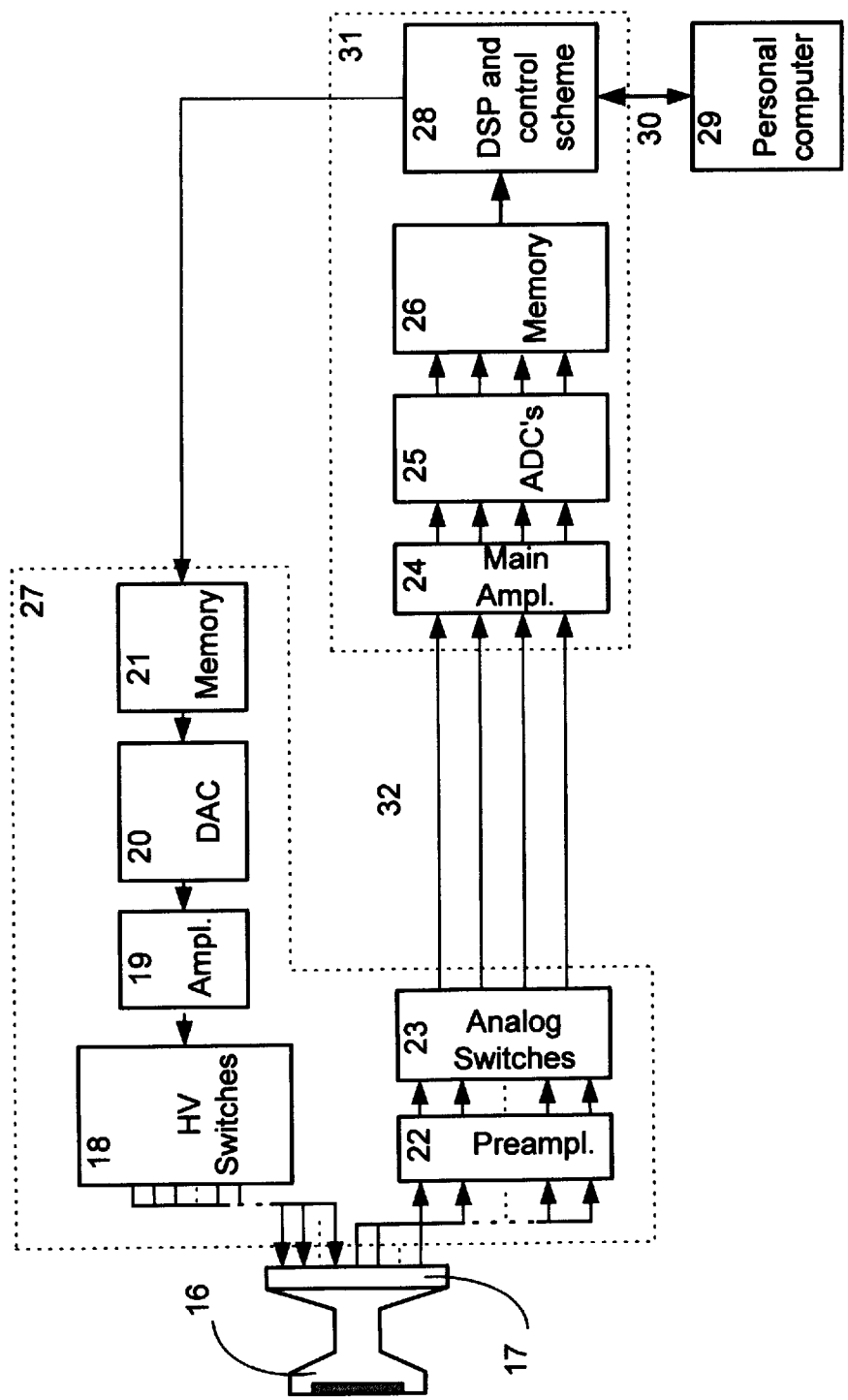
Figure 3.c

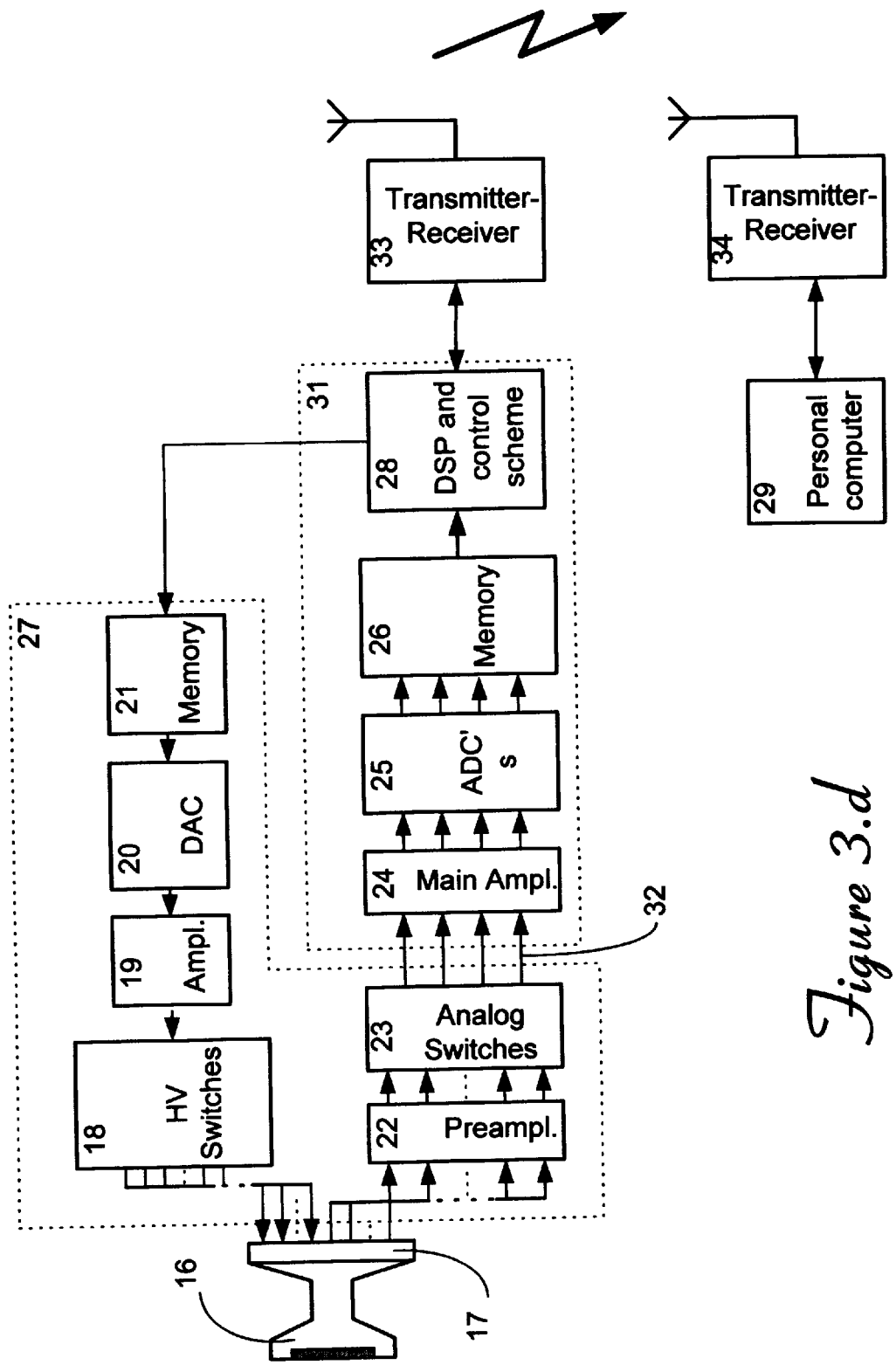
Figure 3.d

METHOD AND APPARATUS FOR FAST ACQUISITION OF ULTRASOUND IMAGES

DESCRIPTION

1. Field of the Invention

The present invention relates to a method and apparatus for fast two and three dimensional ultrasound image acquisition using new apodization functions which reduce the level of side lobe amplitudes and extend the admissible angular range of beam steering.

2. State of the Art

A problem of side lobe amplitudes reduction by the use of apodization functions is discussed in numerous patents, articles and books (see, for example, Gordon S. Kino, Acoustic Waves, Printice-Hall, Englewood, N.J., 07.632, 1987, p. 389). These functions are symmetrical relative to the center of the array and reduce the amplitude of signals for individual elements of the array outlying from the array center. The amplitudes can be generated by transmit array individual elements or they can be amplitudes of echo signals received by receive array individual elements. However, the efficiency of usual apodization functions is low. They reduce the level of side lobe amplitudes in an area nearest to the main beam lobe, but increase the width of the beam. What is more, the reduction of amplitude of the main lobe increases the relative level of side lobe amplitudes in the area far from the beam.

As a result, the main method of beam steering usually used is a shift of transmit and receive apertures along the measured coordinate when the shaped beam is normal to the surface of the transducer and the effect of the beam steering is achieved by the shape of a transducer array. Increasing the field of view and the angular range of a transducer is achieved by using a convex surface of the transducer. Electronic beam steering is used for Doppler measurements of blood velocity, but within a limited angular range, which is possible without the use of any apodization function.

It is very attractive to find some methods or apodization functions which can extend a beam steering range. The size of the transducer and the volume of front-end electronics can be significantly reduced in this instance.

Barabash et. al. (U.S. Pat. No. 5,797,845) discussed a schematic with one transmit transducer element and with crossed geometry of receive arrays which realizes acquisition of three dimensional images by the use of synthetic receive apertures. But, even with the large number of receive transducer individual elements the level of side lobes remains very high. It is clear that the number of transmit elements should be increased and synthetic transmit apertures should be used to provide a shaping of transmit acoustic beam known as 1-st way of shaping of the acoustic beam. Such a method is suggested by Barabash et. al. in patent application Ser. No. 08/910,485 (Batch No. G94) when the formation of a transmit beam is provided by the sequential energizing of different transmit arrays placed in parallel to each other. Reflected echo signals are received by the individual elements of a separate receive array. Echo signal amplitudes are converted and memorized and used for creation of synthetic transmit and receive apertures. A noticeable reduction of side lobe amplitudes can be obtained by increasing the number of phased transmit arrays which will increase the volume of the front-end electronics.

A phased transmit array is the basic unit used for creation of the synthetic transmit aperture in the schematic described above. Bryan et. al. in U.S. Pat. No. 5,673,697 describe a scheme when separate individual elements of a matrix transducer irradiate an investigated volume and reflected echo signals are received by all other individual elements of the matrix. Sequential energizing of different individual elements of the matrix and memorization of reflected echo signals by other individual elements allows one to realize the synthetic transmit and receive apertures and also to reconstruct three dimensional images. The coherent reception of echo signals discussed in this patent is effective for radar technology when a transmit beam shaped by an antenna and for point targets. In the case of a distributed target, as occurs in acoustic technology, we will inevitably obtain some percentage of "ghost" decisions which are defined not only by measurement errors. They are inherent for an acoustic technology because of a non-uniform distributed target with strong fluctuations of acoustic impedance. We can shift these ghost decisions in time and in space by changing some conditions (for example, apodization), but we cannot exclude them completely. Besides, the design of a transducer, suggested in this patent is quite cumbersome.

It is the subject of the present invention to suggest a compact scheme for a personal computer based acoustic scanner for acquisition of two and three dimensional images. Personal computers are used now as part of any modern acoustic scanner. For example, such a system is shown by Daigle R. in U.S. Pat. No. 5,795,297. Parts of an acoustic scanner are connected between each other and a personal computer by an extended personal computer bus when the main functions of information analysis are performed by the personal computer. However, even in such a scheme the author shows, for example, a separate control panel whose functions can be fulfilled by such personal computer tools as a keyboard and mouse. Another serious limitation is the connection of a digital signal processor with the front-end apparatus by a personal computer bus. Digital signal processors were designed to provide fast on-line analysis of information and interface with a personal computer. They use the extended bus for connection with the measurement apparatus. This bus provides faster information exchange than a personal computer bus.

SUMMARY OF INVENTION

This invention consists of a scheme of a compact personal computer based acoustic scanner using synthetic transmit and received apertures which allow us to steer an acoustic beam into a wide range of angles limited only by the irradiation directivity of a transducer individual element. The wide angular range of beam steering is achieved by significantly reducing side lobe amplitudes through use of a complex apodization function. It has three components: a central amplitude apodization function, a time apodization function and a frequency apodization function. All these functions are symmetrical near the center of a transducer array. A central amplitude apodization function can be applied to both transmit and receive arrays. It reduces amplitudes emitted by the central transmit array individual elements. Similarly, it reduces amplitudes of received echo signals for the central receive array individual elements. A time apodization function and a frequency apodization function can be applied to a transmit array only. A time apodization function changes a duration of pulses emitted by transmit array individual elements in accordance with a chosen function symmetrical near the center of the array. A frequency apodization function changes a carrier frequency for different transmit array individual elements and is also symmetrical near the center of the transmit array. Apodization functions are effective if the size of the receive zone near the focus of a synthetic receive aperture is small.

A new concept in the design of acoustic scanners arises from a significant reduction of the side lobe amplitudes, an increased angular acoustic beam steering range, and the ability to create synthetic transmit and receive apertures. This new concept allows us to create a schematic of a compact acoustic scanner. The transmit part of the scanner can have one transmit pulse generator which can be connected with one or more transmit array individual elements. The reception part of the scanner can have one or a group of amplitude analysis electronic channels for reception of echo signals from one or a group of receive array individual elements and can be multiplexed to other receive individual elements or to other groups of receive array individual elements.

The presence of one transmit generator, which can be complex, opens a possibility to realize a wonderful mechanism created by nature, a "bat mechanism" of time compression of pulses. Irradiation of an investigated object by the frequency modulated pulses and a consequent time compression of received echo signals are used in radar technology and significantly increase a signal-noise ratio.

Additionally, a particular decision that reduces side lobe amplitudes for the cross transducer is described in the present invention.

BRIEF DESCRIPTION OF THE DRAWINGS

FIG. 1.*a* shows a flat distribution of amplitudes for the transducer array.

FIG. 1.*b* presents a distribution of amplitudes for the transducer array in accordance with a prior art triangle apodization function.

FIG. 3.*a*, 3.*b* and 3.*c* present different versions of a compact acoustic scanner scheme.

DESCRIPTION

Figure 2:
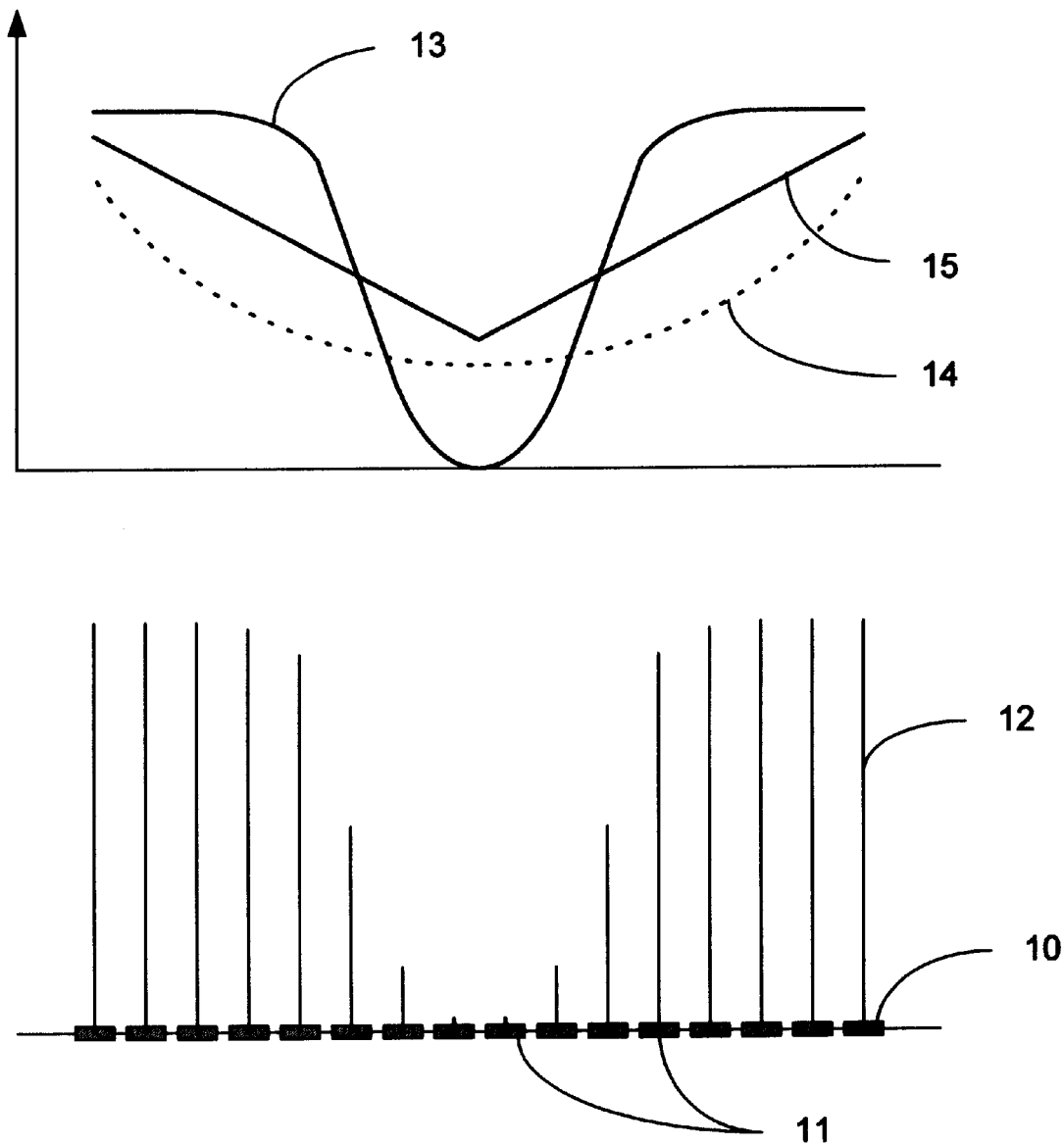
FIG. 2 shows the shape of a central amplitude apodization function, a time apodization function and a frequency apodization function and distribution of amplitudes in accordance with the central amplitude apodization function.

The increase of the signal/noise ratio in acoustic technology is achieved by the summation of echo signal amplitudes. Delays of received echo signals relative to each other cause constructive superposition for signals that are coming from the focal point and cause destructive superposition for signals that are coming from other points of an irradiated target. The following statistical relation is valid in this instance:

$$SNR = A_i * \sqrt{n} / A_{noise}$$

where SNR is a signal/noise ratio, Ai is the echo signal amplitude registered by one electronic channel, n is the number of electronic channels and Anoise is the noise amplitude of one electronic channel.

This relation is valid for independent measurements. The condition for independent measurement is realized by the use of separate independent electronic channels that are dedicated to single array individual elements and measure the echo signal time distribution at the same time. But, measurements will also be independent if they will be done at different times by one electronic channel which is multiplexed to the other array individual elements serially.

Thus, we came to a very simple schematic of an acoustic machine with one transmit and one receive electronic channels. A time T for acquisition of image will be:

$$T = (N_{tr} + N_{rec}) * t_{prop}$$

where Ntr is a number of transmit individual elements, Nrec is the number of receive individual elements and tprop is the propagation time of acoustic waves into an investigated object.

An additional condition for such a simple schematic of an acoustic scanner is that the acquisition time T must be short enough that movement of the investigated object is negligible.

The principal property of this scheme is to have one transmit channel which can be multiplexed to different transmit individual elements. It provides an ability to create synthetic transmit apertures into a wide angular region. The number of receive electronic channels can be increased reasonably to provide a decrease of the acquisition time and a realization of a power of subsequent apparatus such as a digital signal processor (for example 4–8 amplitude analysis channels). Besides, the acoustic radiation dose for the investigated object is reduced significantly, if we will compare a scheme using one generator with a phased transmit array energized by a set of generators.

As seen from the formula for the acquisition time T, if tprop is fixed, T can be decreased by a reduction in the number of transmit Ntr and number of receive Nrec elements only. An effective way to reduce both T and the volume of front-end electronics is to provide a wide angular range of the beam steering with a low level of side lobe amplitudes, instead of the shifting of transmit and received apertures along the measured coordinate.

It is possible to achieve this goal by the use of a central amplitude function, a time apodization function and a frequency apodization function as suggested in this invention.

FIG. 1.*a* shows a flat distribution of amplitudes 12 for individual elements 11 of transducer array 10. Amplitudes 12 are shown conditionally. Amplitudes can belong to acoustic pulses emitted by individual elements of a transmit array, or to echo signals received by individual elements of a receive array.

FIG. 1.*b* presents a prior art triangle apodization function which changes amplitudes for individual elements of a transducer array. The apodization function is symmetrical near the center of the array and reduces amplitudes for outlying individual elements linearly to the ends of the array.

We show the triangle apodization function as an example. It is known many other apodization functions which are also symmetrical near the center of the transducer array, and taking into account errors of a change of amplitudes, differ from each other slightly.

These functions are effective in the area near a main lobe of the acoustic beam and for a long duration of transmit pulses and can be used for a scheme when the steering of the beam is provided by shifting of the transmit and receive apertures along the measured coordinate only.

FIG. 2 presents an exemplary view of a central amplitude apodization function 13, a time apodization function 14 and a frequency apodization function 15. They are also symmetrical near the center of the array. But in contrast to usual apodization functions, a central amplitude apodization function 13 reduces amplitudes 12 of a central section of array individual elements 10. This function can be applied to both transmit and receive arrays.

A time apodization function 14 can be used for transmit array only and changes a duration of emitted pulses. The duration of pulses is short for the central section of transmit array individual elements 11 and increases for individual elements outlying from the center.

A frequency apodization function 15 can be also used for transmit array only and changes a frequency of pulses emitted by transmit array individual elements in accordance with the chosen shape of the apodization function. This apodization function participates in the reduction of side lobe amplitudes and simultaneously increases a time resolution by a time compression of emitted transmit pulses in the focal point.

These apodization functions provide effective rejection of side lobe amplitudes and the extension of a beam steering angular range. For example, high efficiency of the central amplitude apodization function makes it possible to obtain satisfactory parameters of the acoustic beam along a lateral coordinate for 2D transducer with mechanical elevation focussing and with only one transmit individual element. A joint use of the central amplitude apodization function 13, the time apodization function 14 and the frequency apodization function 15 for a simple cross transducer with one transmit and one receive arrays provides effective reduction of side lobe amplitudes within wide limits of angles and allows a realization of a fast acquisition of three dimensional images.

The right choice of the shape of apodization function described above allows us to influence the beam shaping along both lateral and elevation coordinates not only for transducers with a crossed placement of transmit and receive arrays, but even for 2D transducers with mechanical elevation focussing.

Effective reduction of side lobe amplitudes reduces the apparatus volume and allows a design of a portable acoustic scanner for acquisition of two and three dimensional images. A version of an acoustic scanner design with one transmit and one receive channel is shown at FIG. 3.*a*. A transducer head 16 connected with apparatus of the scanner 27 through port 17. Connection is done without a usual cable, the port 17 is placed at the end of a transducer head and has a micro connector and tools for rigid support of said transducer head with apparatus 27. The transmit part of the scanner includes high voltage switches 18 that provide serial connection of different transmit array individual elements to a generator which contains power amplifier 19, digital-analog converter 20 and fast memory 21. A reception part includes preamplifiers 22, analog switches 23, main amplifier 24, analog-digital converter 25 and fast memory 26. Both transmit and reception parts connect with a digital signal processor and control schematic 28 by address and data buses.

A scheme of a generator with fast memory and digital-analog converter provides a wide variety of different waveforms of transmit pulses for energizing of transmit array individual elements. These pulses can have different frequencies and duration, the amplitudes of pulses can be modulated in accordance with a chosen apodization function. The waveform of pulses can have a shape that provides a damping of transducer oscillations after transmission of an acoustic pulse. Transmit pulses are amplified by a power amplifier 19 and multiplexed alternately for different transmit individual elements by high voltage switches 18 and a transducer head port 17. The absence of a cable decreases the capacitive load of the generator and significantly reduces the necessary power of the generator.

A short connection between receive transducer individual elements and the reception part of the apparatus allows us to reduce losses of echo signal amplitudes in comparison with a scheme using a cable connection by factor K:

$$K=(Cc+Ctr)/Ctr,$$

where Cc is the capacitance of the cable used for connection of the receive array individual element with preamplifier for scheme with the cable, Ctr is the capacitance of the receive array individual element.

For a two dimensional image transducer, factor K is equal to 7–10 and is sufficiently greater for three dimensional image transducers with a small array individual element capacitance.

The digital signal processor and control scheme 28 provide a timing of transmit and receive parts of the scanner, loading of information of the waveform of transmit pulses into fast memory 21, and reception of digitized amplitudes of echo signals from fast memory 26.

The digital signal processor provides a fast on line analysis of information including a form of transmit and receive synthetic apertures, calibration and apodization of received digitized echo signal amplitudes for different transmit pulses, summation and spectral analysis of summed digital information, shaping of two and three dimensional images and transmission of information into personal computer 29 by cable 30.

Functions of the personal computer 29 are off line analysis of received information and displaying of reconstructed images. It provides a user interface with apparatus, a control of different parameters and conditions of the measurement of images.

A decrease of the acquisition time of images can be obtained by the reasonable grouping of receive array individual elements and the multiplexing of them. Such a version of acoustic scanner design is shown at FIG. 3.*b*. It differs from the design of FIG. 3.*a* by the increased number of the electronics channels for amplitude analysis of echo signal amplitudes.

Possible reduction of the volume of apparatus for 2D transducers with large area of array individual elements can be done by reduction of preamplifiers 22. Additional reduction of volume of the apparatus can be done excluding fast memories 21 and 26, if the digital signal processor provides necessary frequency in transfer and reception of information.

Another version of acoustic scanner design is shown in FIG. 3.*c*. For this design apparatus for analysis of echo signal amplitudes 31 is separated from the front-end part 27 placed in the handle of the transducer. Connection between the front-end part 27 and the apparatus for analysis of echo signal amplitudes 31 is provided by the cable 32. The apparatus 31 including main amplifiers 24, analog to digital converters 25, fast memory for recording digitized amplitudes of echo signals 26, the digital signal processor and the control scheme 28 and can be made as a separate block connected with a personal computer by the cable 30, or it can be made as a PC card with a common computer bus.

A part of the scanner electronics can be reasonably optimized when placed near the transducer. It can consist of preamplifiers with analog switches (or without analog switches, if the number of channels for analysis of amplitudes of echo pulses is equal to the number of receive array individual elements) and a power amplifier with high voltage switches for multiplexing only transmit array individual elements. The main advantage of such a design is an easily detachable transducer head 16 which can be changed quickly. In particular, it is simple to disinfect such a transducer head.

A procedure of acquisition of acoustic images includes the following steps. An investigated object is irradiated by a transmit pulse emitted by one of the transmit elements. If the transmit pulse is emitted by a transmit element of a small size, it irradiates some solid angle of the investigated object. The three dimensional image acquisition is possible in this case. For transducers with mechanical elevation focus, individual elements have a rectangular shape elongated along the elevation coordinate. So, any individual element is a separate array focused mechanically to some point defined by the radius of curvature of the array element surface. Such elements emit a flat transmit beam and can be used for two dimensional image acquisition only. Reflected echo signals are received by receive individual elements. If this is a small size receive individual element, echo signals will be received from the irradiated solid angle. If the individual element has mechanical elevation focus, a shape of the receive aperture will be flat and echo signals will be received from a sector of the investigated object. Echo signals received by the receive individual element are amplified, digitized and memorized by an electronic channel of amplitude analysis. For a scheme with one amplitude analysis channel (FIG. 3.a) each transmit individual element must emit one transmit pulse for each receive individual element. Every receive individual element must be connected with the amplitude analysis channel by analog switches. The process for one transmit element will be finished when the digitized echo pulse amplitudes are recorded from all receive individual elements. The procedure is repeated by switching the generator output to the next transmit individual element. Each transmit individual element is serially energized, the echo signals are received at every receive individual element, and the echo signal amplitudes from every receive individual element are recorded.

The transmit pulses emitted in series by every transmit individual element have the same amplitude, duration and frequency, and the number of pulses in each series equals the number of receive individual elements. But each transmit individual element emits transmit pulses with amplitude, duration and frequency of pulses defined by the shape of the central amplitude apodization function, the time apodization function and the frequency apodization function, respectively. Amplitudes of transmit pulses are small for central transmit individual elements of the array (some central elements can even be turned off) and increase for individual elements outlying from the center. The time apodization function changes the duration of transmit pulses for different transmit individual elements so that the duration of pulses is short for central elements and increases for elements outlying from the center of the array. The frequency apodization function changes the frequency of pulses emitted by transmit individual elements.

For every transmit individual element a set of digitized amplitude information will be memorized, and each set will have the number of digitized amplitude distributions equal to the number of receive individual elements. The procedure will be finished when digitized echo pulses amplitudes will be recorded from all transmit individual elements.

Acquisition of an image includes the shape of synthetic transmit and receive apertures. Synthetic receive apertures are produced by the phasing of digitized amplitude distributions for different receive individual elements into information sets registered from every transmit individual element. It can be done by shifting of digitized amplitude distributions relative to each other or by an interpolation procedure. Simultaneously, amplitudes of digitized time distributions for different receive individual elements in every information set are changed in accordance with the shape of the central amplitude apodization function which reduces amplitudes for central receive individual elements and increases amplitudes for elements outlying from the center of the array. The shape of the central amplitude apodization function for receive individual elements can be different from the central amplitude apodization function used for transmit individual elements and can be changed for different steering angles. The shape of synthetic receive apertures is the same for all information sets and is defined by the chosen receive focus and steering angle.

Shaping of synthetic transmit apertures is produced by a time alignment of information sets in accordance with the chosen transmit focus and steering angle. A summation of amplitude distributions near the receive focus allows one to obtain a part of acoustic line that is memorized. The change of synthetic transmit and receive apertures with consequent summation of amplitude distributions near other foci and for other receive steering angles allows the acquisition of other parts of the acoustic lines. The joining of recorded parts of acoustic lines creates a two dimensional acoustic image. The change of the steering angle for synthetic transmit apertures allows one to acquire other two dimensional acoustic images and, as a result, to acquire a three dimensional acoustic image.

The shapes of the central amplitude apodization function, the time apodization function, and the frequency apodization function can be changed for different steering angles to optimize the ratio of the main lobe amplitude to side lobe amplitudes.

FIG. 3.d shows a version of the scanner design where a cable 30 for connection with a personal computer is absent. This connection is made by wireless communication using transmitter and receiver 33 placed in the handle of the transducer and transmitter and receiver 34 placed near the personal computer.

The presence of one generator providing complex shaped transmit pulses allows a digital time compression of pulses used for irradiation of an investigated object. A sense of this method is the irradiation of the investigated object by frequency modulated transmit pulses. The duration of transmit pulses can be sufficiently more than usually used. The reflected echo signals have the same duration and frequency modulation. Compression can be obtained by a filtration of different frequency components within known time intervals (because of the known shape of frequency modulated transmit pulses), the phasing of different frequency components and the summation of them. The duration of summed pulses depends on the depth of frequency modulation, sufficiently shorter than transmitted pulses and can be changed for different image modes (2D and 3D modes, Doppler mode) by the change of depth of frequency modulation.

The properties of the generator make it possible to compensate for an attenuation of the high frequency components of transmitted pulses by an increase of high frequency component amplitudes relative to low frequency component amplitudes.

Another advantage of this method is the irradiation of the investigated object by a spectrum of frequencies and, in particular, by low frequencies without a loss of time resolution.

Figure 4:
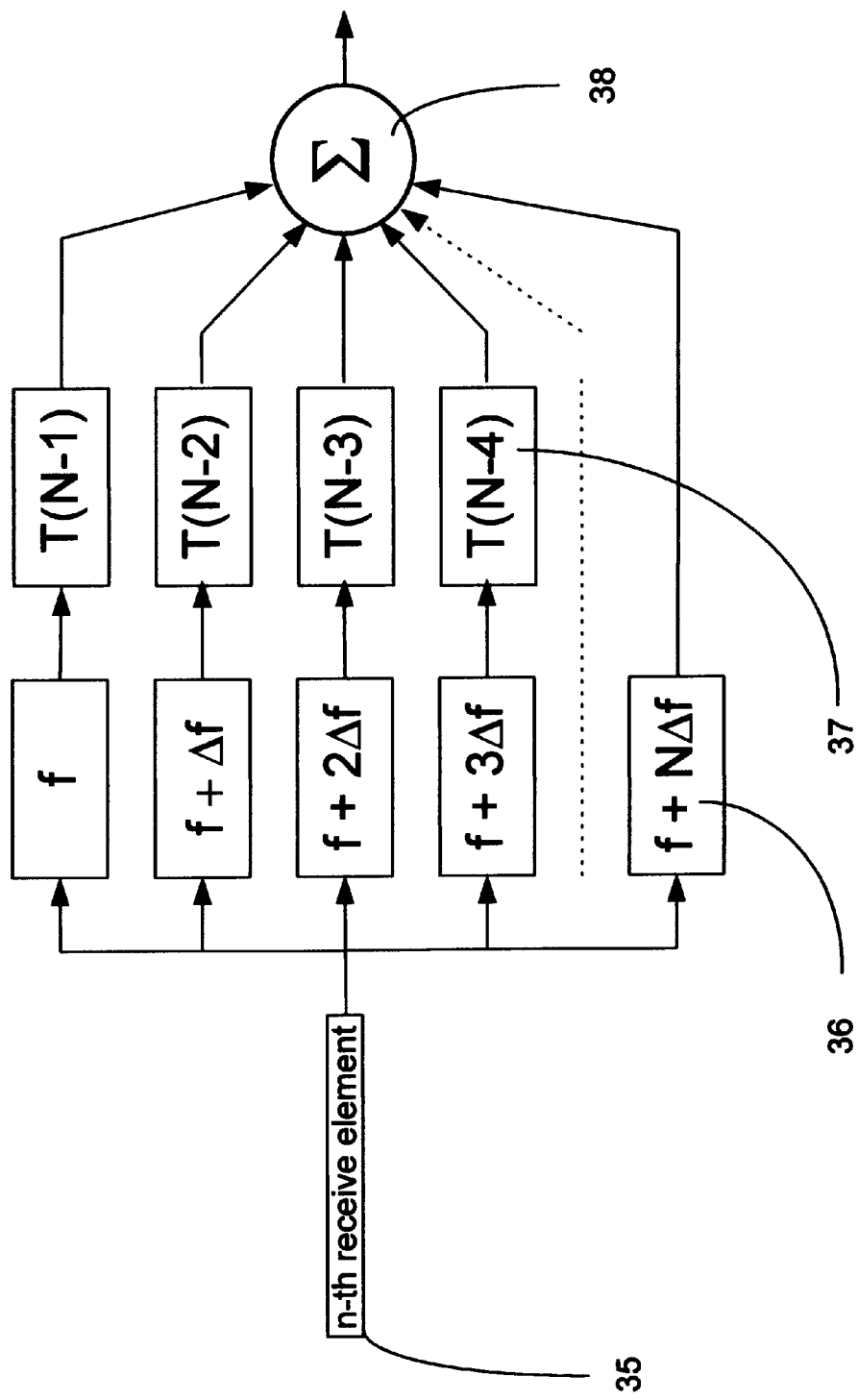
FIG. 4 shows an algorithm of digital time compression of echo signals.

FIG. 4 shows an algorithm of analysis of digitized echo signal information with time compression of echo signals. An example of an analysis of digitized echo signal amplitudes for the n-th receive individual element is shown in the figure. Transmit pulses are frequency modulated within the limits from frequency f at the beginning of the pulse to (f+NΔf) at the end of the pulse. Depth of frequency modulation for this case is equal to NΔf. The frequency modulation function can be linear or otherwise. It is better to use the properties of the generator and provide stepped modulation function with N steps when a frequency is changed by a value of Δf for every step. The time structure of transmit pulses Ttr looks as:

$$Ttr = N\,T,$$

where N is the number of generated frequencies and T is a time of generation for every frequency.

The number of steps N and duration T of generation of every frequency component must be chosen in order to obtain effective filtration and separation of different frequency components.

A digitized echo signal amplitude distribution 35 recorded from n-th receive individual element passes through N digital filters 36. As a result, we will have N amplitude distributions with different frequencies which are shifted in series in time relative to each other for the time interval equal to duration T of the generation of different frequencies. Phasing of amplitude distribution is achieved by serial delay (37) of these distributions for time T relative to each other. Phased amplitude distributions are summed (38). Summation 38 compresses echo signals in time. The shape of compressed echo signals is described by function sin X/X and is shorter than time interval T. Duration of compressed echo pulses depends on the depth of frequency modulation NΔf.

The amplitude of summed pulses Asum is equal to:

$$Asum = N * Ai,$$

where Ai are amplitudes of echo pulses for different frequency components obtained after filtration and N is the number of summed time intervals As seen from the formula above, we can increase the echo signal amplitudes by a factor of N.

The same effect of compression of echo signals can be obtained by the irradiation of the investigated object with N transmit pulses with different frequencies (from f to (f+NΔf)) as was described above. It is not necessary to filter different frequency components in this case, compression of the echo signal will be obtained after summation of amplitude distribution for different receive individual elements n and for different transmit pulses N. Such an approach increases the image time acquisition by a factor of N, but analysis of received information is simpler.

Figure 5:
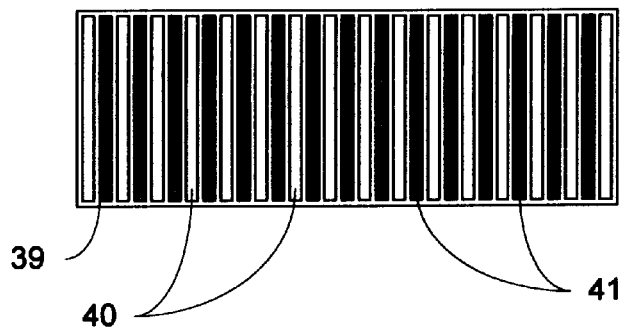
FIG. 5 shows an exemplary view of a transducer for two dimensional image acquisitions.

The same individual elements of array can be used for transmission of acoustic pulses and for reception of echo signals. But, it is better to separate them in transmission and reception modes. A separation of transmit and receive individual elements for a cross geometry of transmit and receive arrays must be done. It provides the ability to acquire three dimensional images. For usual transducers with mechanical elevation focussing and the ability to acquire two dimensional images the separation of individual elements can be done by using, for example, odd individual elements in transmission mode and even individual elements in reception mode (or the opposite case). A version of such a design for a transducer is shown in FIG. 5. Individual elements 40 of array 39 are used as receive elements. They are alternate with elements 41 used as transmit elements that reduces strong influence transmit individual elements for receive elements and improves the noise performance.

Figure 6:
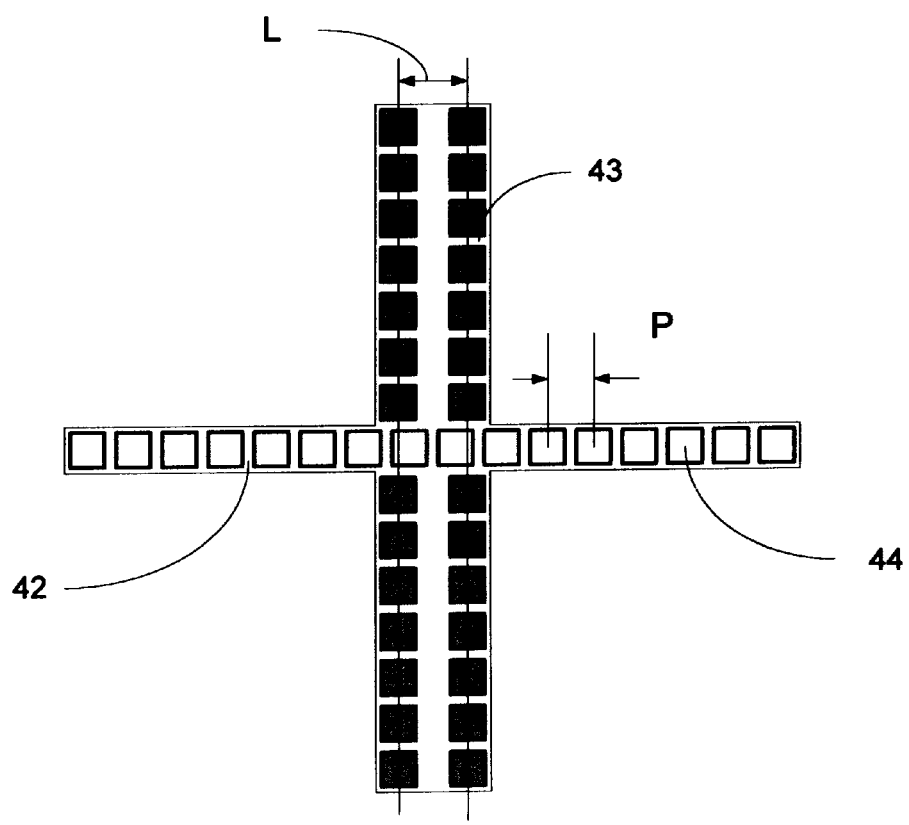
FIG. 6 presents an exemplary view of a cross geometry transducer with two transmit and one receive arrays.

Additional rejection of the level of side lobe amplitudes for cross transducers can be obtained by a special placement of transmit and received arrays. A version of the design of the transducer with two transmit and one receive arrays for three dimensional image acquisition is shown in FIG. 6. Transmit arrays 43 placed normal to receive array 42 with distance L between them is equal to:

$$L = (m + \tfrac{1}{2})P,$$

where P is the pitch of receive array individual elements 44 and m=0,1,2 . . . .

For the transducer of FIG. 6 this step reduces a level of side lobe amplitudes along the coordinate parallel to the receive array significantly. The same reduction of the side lobe amplitudes can be obtained along the coordinate parallel to the transmit arrays by using two receive arrays placed normal to the transmit array with distance L (P is pitch of transmit array individual elements in this case).

What is claimed is:

1. A method of fast acquisition of acoustic images comprising the steps of:

irradiating an investigated object by serial excitation of one of the transmit individual elements by transmit pulses from one generator providing a variety of a waveform for said transmit pulses, receiving the echo signals from said transmit pulses emitted by said one of the transmit individual element by one or a group of receive individual elements, amplification, digitization and memorization of digitized echo signal amplitudes from said one or group of receive individual elements by one or group of amplitude analysis channels, switching of other receive individual elements or other group of receive individual elements to said one or a group of amplitude analysis channels, amplification, digitization and memorization of digitized echo signal amplitudes from said other receive individual elements or other group of receive individual elements, switching of other transmit individual elements to said one generator, irradiating an investigated object by serial excitation of other transmit individual elements by transmit pulses with a changed amplitude, duration and frequency in accordance with a central amplitude apodization function, a time apodization function and a frequency apodization function, receiving the echo signals from said transmit pulses emitted by said other transmit individual elements by said one or group of receive individual elements, amplification, digitization and memorization of digitized echo signal amplitudes from said one or group of receive individual elements by said one or group of amplitude analysis channels, so that said digitized echo signal amplitudes from all receive elements are memorized for every transmit individual element separately, changing said digitized echo signal amplitudes from different receive individual elements in accordance with a central amplitude apodization function, shaping dynamic focused and steered synthetic receive apertures by phasing said digitized echo signal amplitudes from different receive individual elements relative to each other for every said transmit element in accordance with receive foci and receive steering angles, shaping dynamic focused and steered synthetic transmit apertures by phasing said digitized echo signal amplitudes from all receive individual elements for different transmit individual elements relative to each other in accordance with transmit foci and transmit steering angles, acquiring the acoustic lines by summing said digitized echo signal amplitudes from all receive individual elements and for said different transmit individual elements in some time intervals near said receive foci for said receive steering angles, and for different said transmit foci and transmit steering angles, a synthesis of acoustic images by joining said acoustic lines and displaying of said acoustic images.

2. A method of fast acquisition of acoustic images as recited in claim 1 using frequency modulated transmit pulses for irradiating of an investigated object.

3. A method of fast acquisition of acoustic images as recited in claim 1 using a digital filtration of digitized echo signal amplitudes with different frequencies, phasing of them with subsequent summing to obtain the time compressed echo signals.

4. An ultrasound scanner for acquisition of acoustic images comprising:

an ultrasound transducer head having a plurality of transmit and receive individual elements and a port for connection with front-end electronics, a transducer handle having front-end electronics and a connector for connection with said ultrasound transducer head, said front-end electronics having one generator for energizing of transmit individual elements and high voltage switches for connection with one of said transmit individual elements, said one generator for energizing of transmit individual elements having fast memory, digital analog converter and power amplifier placed in said transducer handle and providing a complex shape of transmit pulses for energizing of said transmit individual elements, said front-end electronics having preamplifiers and analog switches placed in said transducer handle and connected with one or group of electronic channels for digitization of echo signal amplitudes, said one or a group of electronic channels for digitization of said echo signal amplitudes having one or a group of main amplifiers and one or a group of analog digital converters with fast memory for amplification, digitization and memorization of said echo signal amplitudes, a digital signal processor and a control scheme for online analysis and acquisition of acoustic images, a personal computer for offline analysis of digitized echo signal amplitudes and displaying of said acoustic images.

5. An ultrasound scanner for acquisition of acoustic images as recited in claim 4 having said one or a group of electronic channels for digitization of said echo signal amplitudes and electronics for online analysis and acquisition of acoustic images are constructed as a separate block connected with a personal computer by a common bus or constructed as a card of a personal computer.

6. An ultrasound scanner for acquisition of acoustic images as recited in claim 4 having an ultrasound transducer head for two dimensional image acquisition with the array of individual elements are made with mechanical elevation focusing, a part of said array individual elements is used for transmission of acoustic pulses into said investigated object, another part is used for reception of echo signals.

7. An ultrasound scanner for acquisition of acoustic images as recited in claim 4 having an ultrasound transducer head for three dimensional image acquisition with more than one transmit arrays and more than one receive arrays, said more than one transmit arrays and said more than one receive arrays having a plurality of transmit and receive individual elements, said transmit arrays placed with distance between them equal to $(m+\frac{1}{2})$ of pitch of said receive individual elements, said receive arrays placed with distance equal to $(m+\frac{1}{2})$ of pitch of said transmit individual elements.

8. An ultrasound scanner for acquisition of acoustic images as recited in claim 4 having wireless connection with a personal computer.

* * * * *